US012588927B2

(12) United States Patent
Baril et al.

(10) Patent No.: US 12,588,927 B2
(45) Date of Patent: Mar. 31, 2026

(54) SURGICAL ACCESS DEVICE WITH FIXATION MECHANISM

(71) Applicant: Covidien LP, Mansfield, MA (US)

(72) Inventors: Jacob C. Baril, Norwalk, CT (US); Kevin C. Desjardin, Prospect, CT (US); Astley C. Lobo, West Haven, CT (US)

(73) Assignee: Covidien LP, Mansfield, MA (US)

( * ) Notice: Subject to any disclaimer, the term of this patent is extended or adjusted under 35 U.S.C. 154(b) by 141 days.

(21) Appl. No.: 18/407,740

(22) Filed: Jan. 9, 2024

(65) Prior Publication Data

US 2024/0138876 A1    May 2, 2024

Related U.S. Application Data

(62) Division of application No. 16/871,277, filed on May 11, 2020, now Pat. No. 11,896,263.

(51) Int. Cl.
*A61B 17/34*        (2006.01)

(52) U.S. Cl.
CPC .. *A61B 17/3423* (2013.01); *A61B 2017/3488* (2013.01)

(58) Field of Classification Search
CPC ............ A61B 17/3417; A61B 17/3421; A61B 17/3423; A61B 17/3431; A61B 2017/3433; A61B 2017/3484; A61B 2017/3488; A61B 2017/3492; A61M 25/04; A61M 2025/0233
See application file for complete search history.

(56) References Cited

U.S. PATENT DOCUMENTS

| | | | |
|---|---|---|---|
| 397,060 | A | 1/1889 | Knapp |
| 512,456 | A | 1/1894 | Sadikova |
| 1,213,005 | A | 1/1917 | Pillsbury |
| 2,556,783 | A * | 6/1951 | Wallace ................. A61B 17/22 606/127 |
| 2,912,981 | A | 11/1959 | Keough |
| 2,936,760 | A | 5/1960 | Gains |

(Continued)

FOREIGN PATENT DOCUMENTS

| | | |
|---|---|---|
| EP | 0480653 A1 | 4/1992 |
| EP | 0610099 A2 | 8/1994 |

(Continued)

*Primary Examiner* — Diane D Yabut
(74) *Attorney, Agent, or Firm* — Dymera IP, LLC

(57)        ABSTRACT

A surgical access device includes a cannula body and a fixation mechanism. The fixation mechanism includes a collar, a driver, a distal ring, a proximal ring, and a plurality of petals. The driver extends distally from the collar, and the distal ring is operatively engaged with a distal portion of the driver. The proximal ring at least partially surrounds an elongated portion of the cannula body and is disposed proximally of the distal ring. The plurality of petals extends proximally from the distal ring and is longitudinally translatable relative to the proximal ring. Longitudinal translation of the collar causes the plurality of petals to move between a first position defining a first gap between a proximal end of the plurality of petals and the elongated portion, and a second position defining a second, greater gap between the proximal end of the plurality of petals and the elongated portion.

14 Claims, 13 Drawing Sheets

(56)          References Cited

U.S. PATENT DOCUMENTS

| | | | |
|---|---|---|---|
| 3,039,468 | A | 6/1962 | Price |
| 3,050,066 | A | 8/1962 | Koehn |
| 3,253,594 | A | 5/1966 | Matthews et al. |
| 3,397,699 | A | 8/1968 | Kohl |
| 3,545,443 | A | 12/1970 | Ansari et al. |
| 3,713,447 | A | 1/1973 | Adair |
| 3,774,596 | A | 11/1973 | Cook |
| 3,800,788 | A | 4/1974 | White |
| 3,882,852 | A | 5/1975 | Sinnreich |
| 3,896,816 | A | 7/1975 | Mattler |
| 3,961,632 | A | 6/1976 | Moossun |
| RE29,207 | E | 5/1977 | Bolduc et al. |
| 4,083,369 | A | 4/1978 | Sinnreich |
| 4,217,889 | A | 8/1980 | Radovan et al. |
| 4,243,050 | A | 1/1981 | Littleford |
| 4,276,874 | A | 7/1981 | Wolvek et al. |
| 4,312,353 | A | 1/1982 | Shahbabian |
| 4,327,709 | A | 5/1982 | Hanson et al. |
| 4,345,606 | A | 8/1982 | Littleford |
| 4,411,654 | A | 10/1983 | Boarini et al. |
| 4,416,267 | A | 11/1983 | Garren et al. |
| 4,490,137 | A | 12/1984 | Moukheibir |
| 4,496,345 | A | 1/1985 | Hasson |
| 4,574,806 | A | 3/1986 | McCarthy |
| 4,581,025 | A | 4/1986 | Timmermans |
| 4,596,554 | A | 6/1986 | Dastgeer |
| 4,596,559 | A | 6/1986 | Fleischhacker |
| 4,608,965 | A | 9/1986 | Anspach, Jr. et al. |
| 4,644,936 | A | 2/1987 | Schiff |
| 4,654,030 | A | 3/1987 | Moll et al. |
| 4,685,447 | A | 8/1987 | Iversen et al. |
| 4,701,163 | A | 10/1987 | Parks |
| 4,738,666 | A | 4/1988 | Fuqua |
| 4,769,038 | A | 9/1988 | Bendavid et al. |
| 4,772,266 | A | 9/1988 | Groshong |
| 4,779,611 | A | 10/1988 | Grooters et al. |
| 4,784,133 | A | 11/1988 | Mackin |
| 4,793,348 | A | 12/1988 | Palmaz |
| 4,798,205 | A | 1/1989 | Bonomo et al. |
| 4,800,901 | A | 1/1989 | Rosenberg |
| 4,802,479 | A | 2/1989 | Haber et al. |
| 4,813,429 | A | 3/1989 | Eshel et al. |
| 4,840,613 | A | 6/1989 | Balbierz |
| 4,854,316 | A | 8/1989 | Davis |
| 4,861,334 | A | 8/1989 | Nawaz |
| 4,865,593 | A | 9/1989 | Ogawa et al. |
| 4,869,717 | A | 9/1989 | Adair |
| 4,888,000 | A | 12/1989 | McQuilkin et al. |
| 4,899,747 | A | 2/1990 | Garren et al. |
| 4,917,668 | A | 4/1990 | Haindl |
| 4,931,042 | A | 6/1990 | Holmes et al. |
| 4,955,895 | A | 9/1990 | Sugiyama et al. |
| 5,002,557 | A | 3/1991 | Hasson |
| 5,009,643 | A | 4/1991 | Reich et al. |
| 5,030,206 | A | 7/1991 | Lander |
| 5,030,227 | A | 7/1991 | Rosenbluth et al. |
| 5,074,871 | A | 12/1991 | Groshong |
| 5,098,392 | A | 3/1992 | Fleischhacker et al. |
| 5,104,383 | A | 4/1992 | Shichman |
| 5,116,318 | A | 5/1992 | Hillstead |
| 5,116,357 | A | 5/1992 | Eberbach |
| 5,122,122 | A | 6/1992 | Allgood |
| 5,122,155 | A | 6/1992 | Eberbach |
| 5,137,512 | A | 8/1992 | Burns et al. |
| 5,141,494 | A | 8/1992 | Danforth et al. |
| 5,141,515 | A | 8/1992 | Eberbach |
| 5,147,302 | A | 9/1992 | Euteneuer et al. |
| 5,147,316 | A | 9/1992 | Castillenti |
| 5,147,374 | A | 9/1992 | Fernandez |
| 5,158,545 | A | 10/1992 | Trudell et al. |
| 5,159,925 | A | 11/1992 | Neuwirth et al. |
| 5,163,949 | A | 11/1992 | Bonutti |
| 5,176,692 | A | 1/1993 | Wilk et al. |
| 5,176,697 | A | 1/1993 | Hasson |
| 5,183,463 | A | 2/1993 | Debbas |
| 5,188,596 | A | 2/1993 | Condon et al. |
| 5,188,630 | A | 2/1993 | Christoudias |
| 5,195,507 | A | 3/1993 | Bilweis |
| 5,197,971 | A | * | 3/1993 | Bonutti ............. A61B 17/0218 |
| | | | | 604/164.11 |
| 5,201,742 | A | 4/1993 | Hasson |
| 5,201,754 | A | 4/1993 | Crittenden et al. |
| 5,209,725 | A | 5/1993 | Roth |
| 5,215,526 | A | 6/1993 | Deniega et al. |
| 5,222,970 | A | 6/1993 | Reeves |
| 5,226,890 | A | 7/1993 | Ianniruberto et al. |
| 5,232,446 | A | 8/1993 | Arney |
| 5,232,451 | A | * | 8/1993 | Freitas .................. A61B 17/34 |
| | | | | 604/174 |
| 5,234,454 | A | 8/1993 | Bangs |
| 5,250,025 | A | 10/1993 | Sosnowski et al. |
| 5,258,026 | A | 11/1993 | Johnson et al. |
| 5,269,753 | A | 12/1993 | Wilk |
| 5,290,249 | A | * | 3/1994 | Foster .................... A61B 17/34 |
| | | | | 604/174 |
| 5,308,327 | A | 5/1994 | Heaven et al. |
| 5,309,896 | A | 5/1994 | Moll et al. |
| 5,314,443 | A | 5/1994 | Rudnick |
| 5,318,012 | A | 6/1994 | Wilk |
| 5,330,497 | A | 7/1994 | Freitas et al. |
| 5,342,307 | A | 8/1994 | Euteneuer et al. |
| 5,346,504 | A | 9/1994 | Ortiz et al. |
| 5,359,995 | A | 11/1994 | Sewell, Jr. |
| 5,361,752 | A | 11/1994 | Moll et al. |
| 5,370,134 | A | 12/1994 | Chin et al. |
| 5,383,889 | A | 1/1995 | Warner et al. |
| 5,397,311 | A | 3/1995 | Walker et al. |
| 5,402,772 | A | 4/1995 | Moll et al. |
| 5,407,433 | A | 4/1995 | Loomas |
| 5,431,173 | A | 7/1995 | Chin et al. |
| 5,445,615 | A | 8/1995 | Yoon |
| 5,468,248 | A | 11/1995 | Chin et al. |
| 5,514,091 | A | 5/1996 | Yoon |
| 5,514,153 | A | 5/1996 | Bonutti |
| 5,540,658 | A | 7/1996 | Evans et al. |
| 5,540,711 | A | 7/1996 | Kieturakis et al. |
| 5,607,441 | A | 3/1997 | Sierocuk et al. |
| 5,607,443 | A | 3/1997 | Kieturakis et al. |
| 5,632,761 | A | 5/1997 | Smith et al. |
| 5,656,013 | A | 8/1997 | Yoon |
| 5,667,479 | A | 9/1997 | Kieturakis |
| 5,667,520 | A | 9/1997 | Bonutti |
| 5,704,372 | A | 1/1998 | Moll et al. |
| 5,707,382 | A | 1/1998 | Sierocuk et al. |
| 5,713,869 | A | 2/1998 | Morejon |
| 5,722,986 | A | 3/1998 | Smith et al. |
| 5,728,119 | A | 3/1998 | Smith et al. |
| 5,730,748 | A | 3/1998 | Fogarty et al. |
| 5,730,756 | A | 3/1998 | Kieturakis et al. |
| 5,738,628 | A | 4/1998 | Sierocuk et al. |
| 5,749,539 | A | 5/1998 | Ratzel et al. |
| 5,755,693 | A | 5/1998 | Walker et al. |
| 5,762,604 | A | 6/1998 | Kieturakis |
| 5,772,680 | A | 6/1998 | Kieturakis et al. |
| 5,779,728 | A | 7/1998 | Lunsford et al. |
| 5,797,947 | A | 8/1998 | Mollenauer |
| 5,803,901 | A | 9/1998 | Chin et al. |
| 5,810,867 | A | 9/1998 | Zarbatany et al. |
| 5,814,060 | A | 9/1998 | Fogarty et al. |
| 5,836,913 | A | 11/1998 | Orth et al. |
| 5,836,961 | A | 11/1998 | Kieturakis et al. |
| 5,865,802 | A | 2/1999 | Yoon et al. |
| 5,893,866 | A | 4/1999 | Hermann et al. |
| 5,925,058 | A | 7/1999 | Smith et al. |
| 6,361,543 | B1 | 3/2002 | Chin et al. |
| 6,368,337 | B1 | 4/2002 | Kieturakis et al. |
| 6,375,665 | B1 | 4/2002 | Nash et al. |
| 6,379,372 | B1 | 4/2002 | Dehdashtian et al. |
| 6,432,121 | B1 | 8/2002 | Jervis |
| 6,447,529 | B2 | 9/2002 | Fogarty et al. |
| 6,468,205 | B1 | 10/2002 | Mollenauer et al. |
| 6,506,200 | B1 | 1/2003 | Chin |
| 6,514,272 | B1 | 2/2003 | Kieturakis et al. |
| 6,517,514 | B1 | 2/2003 | Campbell |

(56)         References Cited

U.S. PATENT DOCUMENTS

| 6,527,787 | B1 | 3/2003 | Fogarty et al. |
| 6,540,764 | B1 | 4/2003 | Kieturakis et al. |
| 6,796,960 | B2 | 9/2004 | Cioanta et al. |
| 8,454,645 | B2 | 6/2013 | Criscuolo et al. |
| 10,751,086 | B2 | 8/2020 | Shipp et al. |
| 11,896,263 | B2 | 2/2024 | Baril et al. |
| 2005/0187578 | A1 | 8/2005 | Rosenberg et al. |
| 2019/0307486 | A1* | 10/2019 | Buyda ................ A61B 17/3462 |

FOREIGN PATENT DOCUMENTS

| EP | 0880939 | A1 | 12/1998 |
| WO | 9206638 | A1 | 4/1992 |
| WO | 9218056 | A1 | 10/1992 |
| WO | 9221293 | A1 | 12/1992 |
| WO | 9221295 | A1 | 12/1992 |
| WO | 9309722 | A1 | 5/1993 |
| WO | 9721461 | A1 | 6/1997 |
| WO | 9912602 | A1 | 3/1999 |
| WO | 0126724 | A2 | 4/2001 |
| WO | 02096307 | A2 | 12/2002 |
| WO | 2004032756 | A2 | 4/2004 |

* cited by examiner

SURGICAL ACCESS DEVICE WITH FIXATION MECHANISM

CROSS-REFERENCE TO RELATED APPLICATION

This application is a divisional application of U.S. patent application Ser. No. 16/871,277, filed on May 11, 2020, the entire contents of which are incorporated by reference herein.

BACKGROUND

The present disclosure relates to a surgical access device. More particularly, the present disclosure relates to a surgical access device having a fixation mechanism to help maintain its position relative to a patient during a surgical procedure.

In minimally invasive surgical procedures, including endoscopic and laparoscopic surgeries, a surgical access device permits the introduction of a variety of surgical instruments into a body cavity or opening. A surgical access device (e.g., a cannula) is introduced through an opening in tissue (i.e., a naturally occurring orifice or an incision) to provide access to an underlying surgical site in the body. The incision is typically made using an obturator having a blunt or sharp tip that has been inserted within the passageway of the surgical access device. For example, a cannula has a tube of rigid material with a thin wall construction, through which an obturator may be passed. The obturator is utilized to penetrate a body wall, such as an abdominal wall, or to introduce the surgical access device through the body wall and is then removed to permit introduction of surgical instrumentation through the surgical access device to perform the surgical procedure.

During these procedures, it may be challenging to maintain the position of the surgical access device with respect to the body wall, particularly when exposed to a pressurized environment. To help maintain the position of the surgical access device with respect to the body wall, an expandable anchor or fixation mechanism disposed near a distal end of the surgical access device is occasionally used. Expanding such an anchor while the surgical access device is within the body helps prevent the surgical access device from undesired movement with respect to the body.

Accordingly, it may be helpful to provide a non-inflatable fixation mechanism, as opposed to one that uses a balloon, for instance, to help maintain the longitudinal position of the surgical access device with respect to the patient.

SUMMARY

The present disclosure relates to a surgical access device including a cannula body and a fixation mechanism. The cannula body includes a housing and an elongated portion extending distally from the housing. The elongated portion defines a longitudinal axis and defines a channel extending therethrough. The fixation mechanism is disposed in mechanical cooperation with the elongated portion of the cannula body, and includes a collar, a driver, a distal ring, a proximal ring, and a plurality of petals. The collar at least partially surrounds a portion of the elongated portion of the cannula body and is longitudinally translatable relative to the elongated portion of the cannula body. The driver extends distally from the collar. The distal ring is operatively engaged with a distal portion of the driver. The proximal ring at least partially surrounds the elongated portion of the cannula body and is disposed proximally of the distal ring.

The plurality of petals extends proximally from the distal ring and is longitudinally translatable relative to the proximal ring. Longitudinal translation of the collar relative to the elongated portion of the cannula body causes the plurality of petals to move between a first position defining a first gap between a proximal end of the plurality of petals and the elongated portion of the cannula body, and a second position defining a second gap between the proximal end of the plurality of petals and the elongated portion of the cannula body. The second gap is greater than the first gap.

In aspects, proximal translation of the collar relative to the elongated portion of the cannula body may cause the plurality of petals to move from the first position to the second position.

In other aspects, the collar may be rotatable about the longitudinal axis relative to the elongated portion of the cannula body.

In further aspects, the driver may be fixed from moving longitudinally relative to the collar, and the driver may be fixed from rotation about the longitudinal axis relative to the collar.

In disclosed aspects, the driver may be fixed from moving longitudinally relative to the distal ring, and the driver may be fixed from rotation about the longitudinal axis relative to the distal ring.

In aspects, the proximal ring may be fixed from moving longitudinally relative to the elongated portion of the cannula body. The proximal ring may be fixed from rotation about the longitudinal axis relative to the elongated portion of the cannula body.

In other aspects, each petal of the plurality of petals may include a hook configured to engage the proximal ring when the plurality of petals is in the first position. The hook of each petal of the plurality of petals may be configured to be free from contact with the proximal ring when the plurality of petals is in the second position.

In further aspects, the proximal end of the plurality of petals may be biased away from the longitudinal axis.

In disclosed aspects, the collar may include a slot configured to slidingly engage a pin on the elongated portion of the cannula body. The slot may include a proximal portion, a distal portion, and a connecting portion interconnecting the proximal portion and the distal portion. The connecting portion of the slot may be laterally offset from the proximal portion of the slot and the distal portion of the slot. The connecting portion of the slot may be parallel to the longitudinal axis.

The present disclosure also relates to a fixation mechanism for use with a surgical access device. The fixation mechanism includes a collar, a driver, a distal ring, a plurality of petals, and a proximal ring. The collar defines a passageway therethrough, which defines a longitudinal axis. The driver extends distally from the collar. The distal ring is operatively engaged with a distal portion of the driver. The proximal ring radially surrounds a portion of the driver and is disposed proximally of the distal ring. The plurality of petals extends proximally from the distal ring. The proximal ring surrounds portions of the plurality of petals and is disposed proximally of the distal ring. The plurality of petals is longitudinally translatable relative to the proximal ring. Proximal translation of the collar relative to the proximal ring causes the plurality of petals to move from a first position defining a first gap between a proximal end of the plurality of petals and the proximal ring, to a second position defining a second gap between the proximal end of the plurality of petals and the proximal ring. The second gap is greater than the first gap.

In aspects, the proximal end of the plurality of petals may be in contact with the proximal ring when the plurality of petals is in the first position. The proximal end of the plurality of petals may be free from contact with the proximal ring when the plurality of petals is in the second position.

The present disclosure also relates to a surgical access device including a cannula body, and a fixation mechanism. The cannula body includes a housing and an elongated portion extending distally from the housing. The cannula body defines a longitudinal axis, defines a channel extending therethrough, and includes a pin extending therefrom. The fixation mechanism is disposed in mechanical cooperation with the elongated portion of the cannula body, and includes a collar, a sleeve, an expandable member, and a distal ring. The collar at least partially surrounds a portion of the elongated portion of the cannula body, is longitudinally translatable relative to the elongated portion of the cannula body, and is rotatable about the longitudinal axis relative to the elongated portion of the cannula body. The collar includes a cam surface which slidingly engages the pin of the cannula body. The sleeve extends distally from the collar. The expandable member extends distally from the sleeve and radially surrounds a portion of the elongated portion of the cannula body. The distal ring is engaged with a distal portion of the expandable member and is fixed from longitudinal translation relative to the elongated portion of the cannula body. Distal translation of the collar relative to the elongated portion of the cannula body causes the expandable member to move from a first position defining a first gap between a middle portion of the expandable and the elongated portion of the cannula body, to a second position defining a second gap between the middle portion of the expandable member and the elongated portion of the cannula body. The second gap is greater than the first gap.

In aspects, the expandable member may be made out of rubber.

In further aspects, the expandable member may non-inflatably transition between the first position and the second position.

In additional aspects, the distal translation and a simultaneous rotation of the collar about the longitudinal axis relative to the elongated portion of the cannula body may cause the expandable member to move from the first position to the second position.

In disclosed aspects, the cam surface of the collar may include a proximal portion having a valley, an angled connecting portion, and a distal portion. The distal portion of the cam surface may contact the pin of the elongated portion of the cannula body when the expandable member is in the first position.

DESCRIPTION OF THE DRAWINGS

Various aspects of the present disclosure are illustrated herein with reference to the accompanying drawings, wherein.

DETAILED DESCRIPTION

Figure 1:
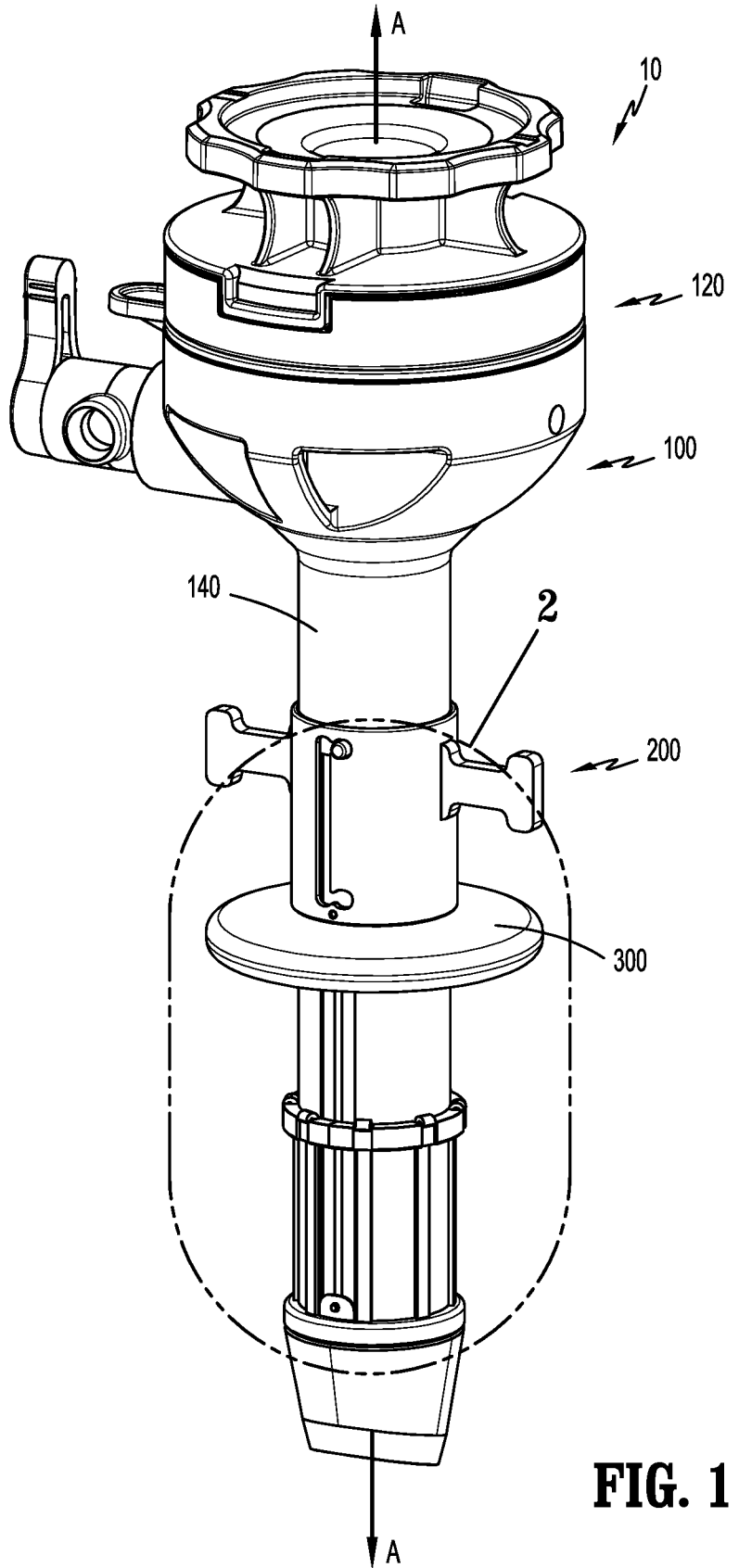
FIG. 1 is a perspective view of a surgical access device illustrating a fixation member in an undeployed configuration in accordance with a first aspect of the present disclosure.

Aspects of the presently disclosed surgical access device will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component farther away from the user.

Generally, the surgical access device or cannula, often part of a trocar assembly, may be employed during surgery (e.g., laparoscopic surgery) and may, in various aspects, provide for the sealed access of laparoscopic surgical instruments into an insufflated body cavity, such as the abdominal cavity. The cannula is usable with an obturator insertable therethrough. The cannula and obturator are separate components but are capable of being selectively connected together. For example, the obturator may be inserted into and through the cannula until the handle of the obturator engages, e.g., selectively locks into, a proximal housing of the cannula. In this initial configuration, the trocar assembly is employed to tunnel through an anatomical structure, e.g., the abdominal wall, either by making a new passage through the structure or by passing through an existing opening through the structure. Once the trocar assembly has tunneled through the anatomical structure, the obturator is removed, leaving the cannula in place in the structure, e.g., in the incision created by the trocar assembly. The proximal housing of the cannula may include seals or valves that prevent the escape of insufflation gases from the body cavity, while also allowing surgical instruments to be inserted into the body cavity.

FIGS. 1-8 illustrate a first aspect of a surgical access device according to the present disclosure. With initial reference to FIG. 1, the surgical access device 10 includes a cannula body 100 and a fixation mechanism 200. The cannula body 100 includes a proximal housing 120 at its proximal end and includes an elongated portion 140 extending distally from the proximal housing 120. The elongated portion 140 defines a channel 150 (FIG. 3) extending therethrough, and defines a longitudinal axis "A-A." A seal assembly 160 (FIG. 3) is housed at least partially within the proximal housing 120. An obturator (not shown) is insertable through the channel 150 and is engageable with the proximal housing 120, for instance. Additionally, while the fixation mechanism 200 is shown in connection with the surgical access device 10, the fixation mechanism 200 of the present disclosure can also be used with other types of surgical instruments.

Figure 2:
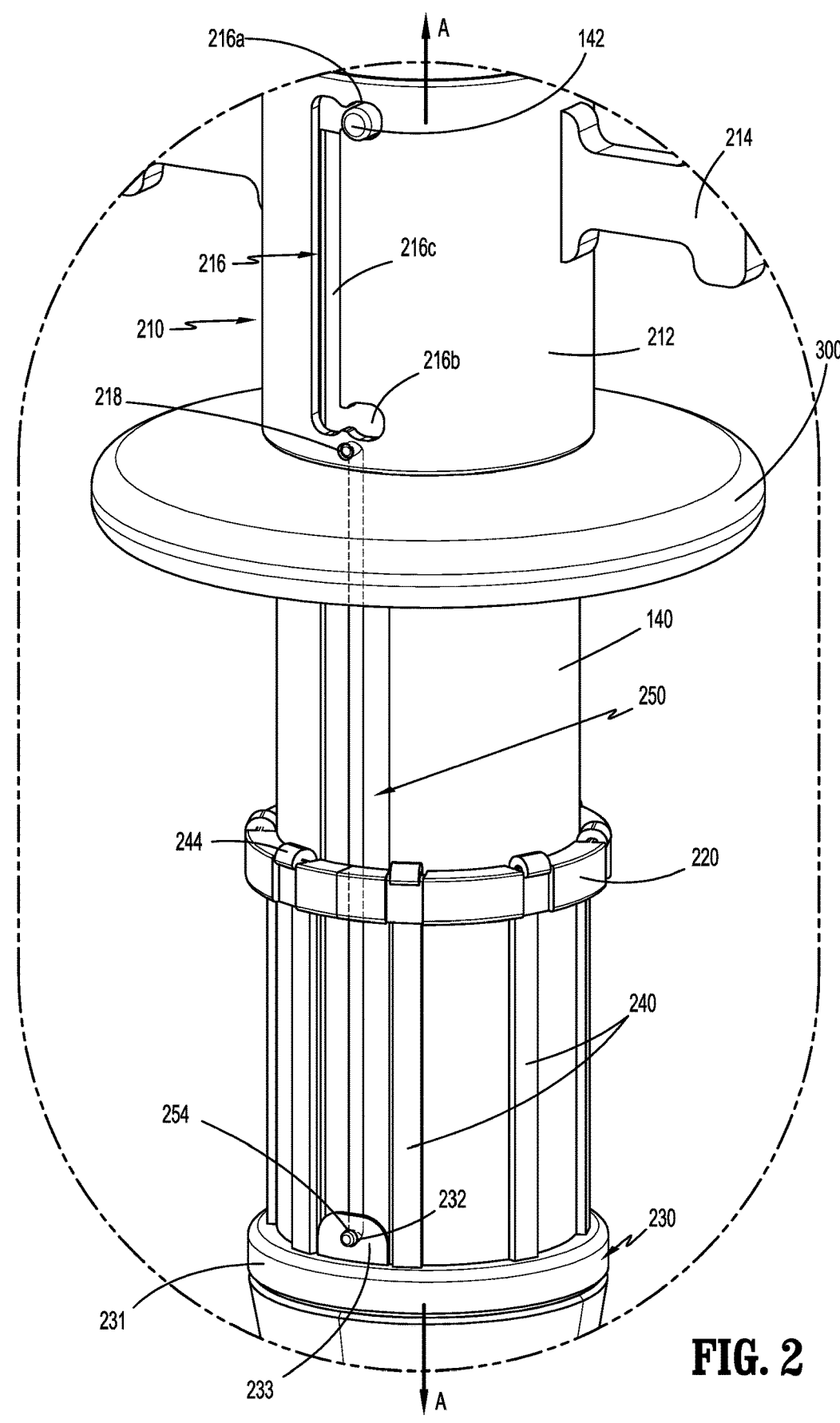
FIG. 2 is an enlarged view of the area of detail indicated in FIG. 1.
Figure 4:
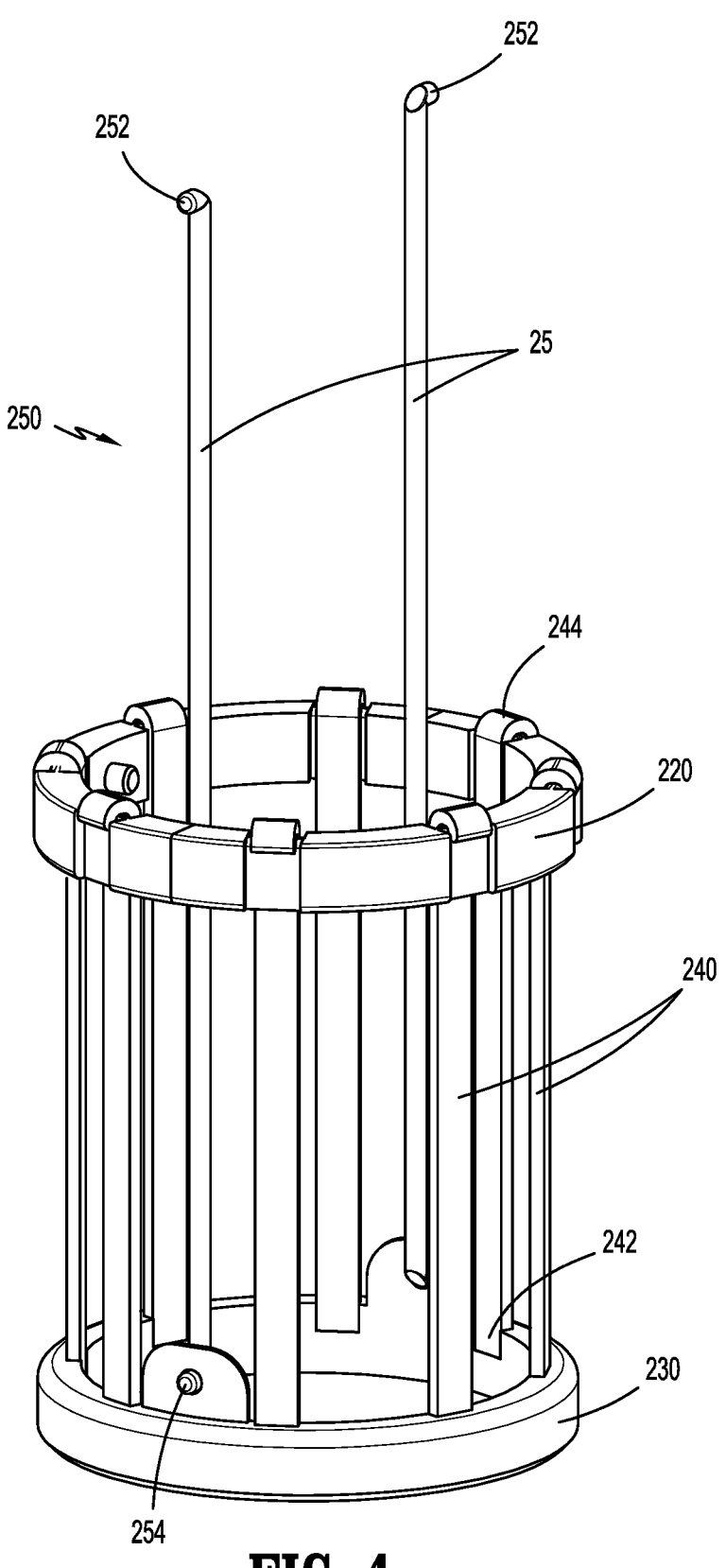
FIG. 4 is a perspective view of a portion of a fixation assembly of the surgical access device of FIG. 1.
Figure 5:
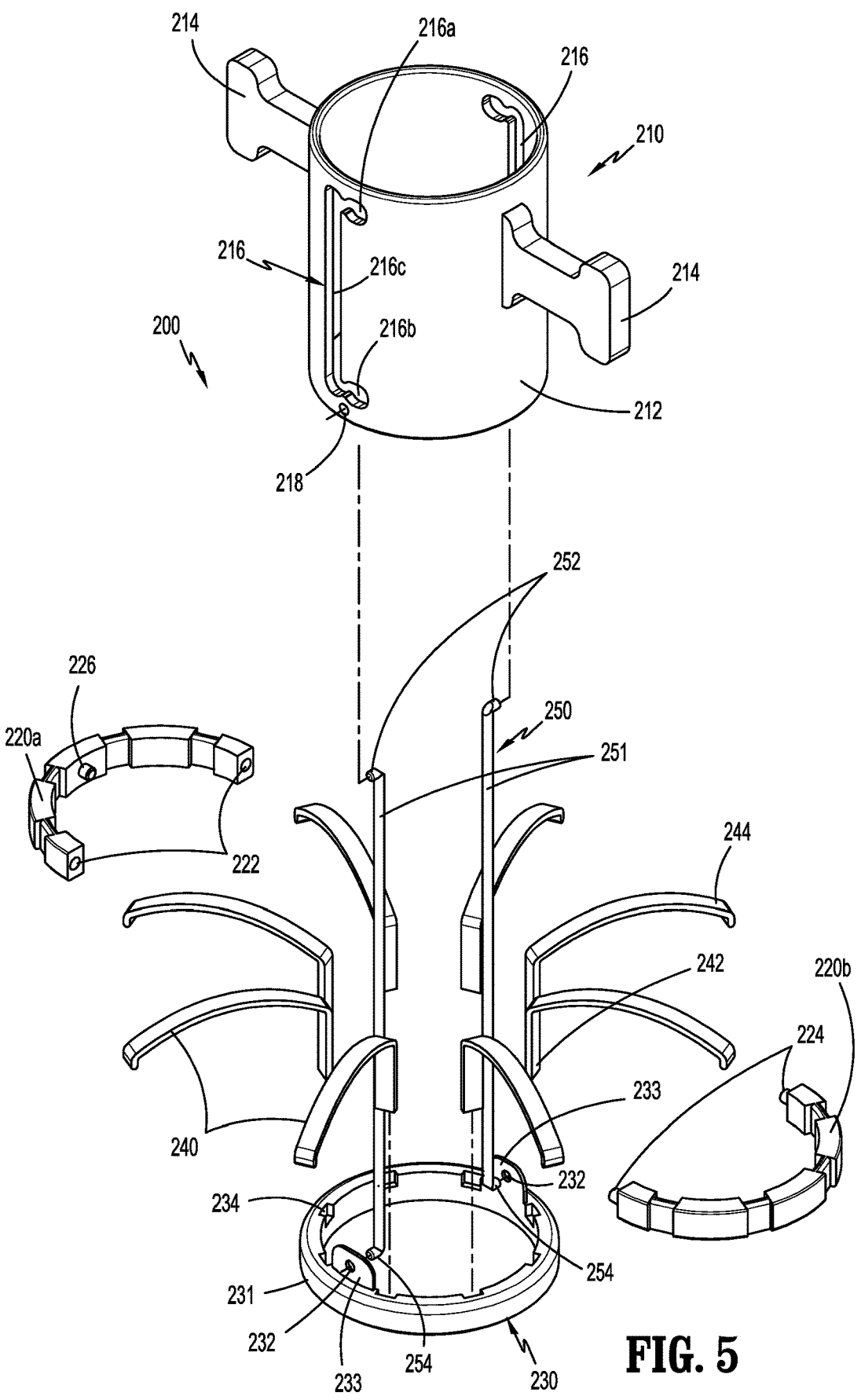
FIG. 5 is an assembly view of the fixation assembly of the surgical access device of FIG. 1.

With particular reference to FIGS. 2, 4, and 5, the fixation mechanism 200 is disposed in mechanical cooperation with the elongated portion 140 of the cannula body 100, and includes a collar 210, a proximal ring 220, a distal ring 230, a plurality of petals 240, and a driver 250. Generally, the collar 210 is positioned such that it radially surrounds a portion of the elongated portion 140 of the cannula body 100. The driver 250 extends distally from the collar 210 and is coupled to the distal ring 230. The plurality of petals 240 extends proximally from the distal ring 230. The proximal ring 220 is coupled to the elongated portion 140 of the cannula body 100 and radially surrounds portions of the plurality of petals 240.

More particularly, and with reference to FIGS. 2-5, the collar 210 is a ring-like structure that radially surrounds a portion of the elongated portion 140 of the cannula body 100 and is longitudinally translatable relative thereto. The collar 210 includes a body 212, a pair of flanges 214 extending radially outward from the body 212, a pair of slots 216, and a pair of apertures 218 (only a single aperture 218 is visible in the figures). The flanges 214 are configured to be grasped by a user to facilitate rotating the collar 210 about the longitudinal axis "A-A," and to facilitate translating the collar 210 longitudinally in a direction parallel to the longitudinal axis "A-A."

Each slot of the pair of slots 216 of the collar 210 is configured to slidingly engage a respective pin 142 (FIGS. 2 and 3) extending radially outward from the elongated portion 140 of the cannula body 100. Each slot of the pair of slots 216 includes a proximal portion 216a, a distal portion 216b, and a connecting portion 216c, which interconnects the proximal portion 216a and the distal portion 216b (FIGS. 2 and 5). Rotation and proximal translation of the collar 210 relative to the elongated portion 140 causes the pair of slots 216 to move relative to the pins 142 from a first position where each pin 142 is within the proximal portion 216a of each slot 216 (FIGS. 2 and 6), which corresponds to the plurality of petals 240 being in the first position (discussed in detail below), to a second position where each pin 142 is within the distal portion 216b of each slot 216 (FIGS. 7 and 8), which corresponds to the plurality of petals 240 being in the second position (discussed in detail below).

Figure 3:
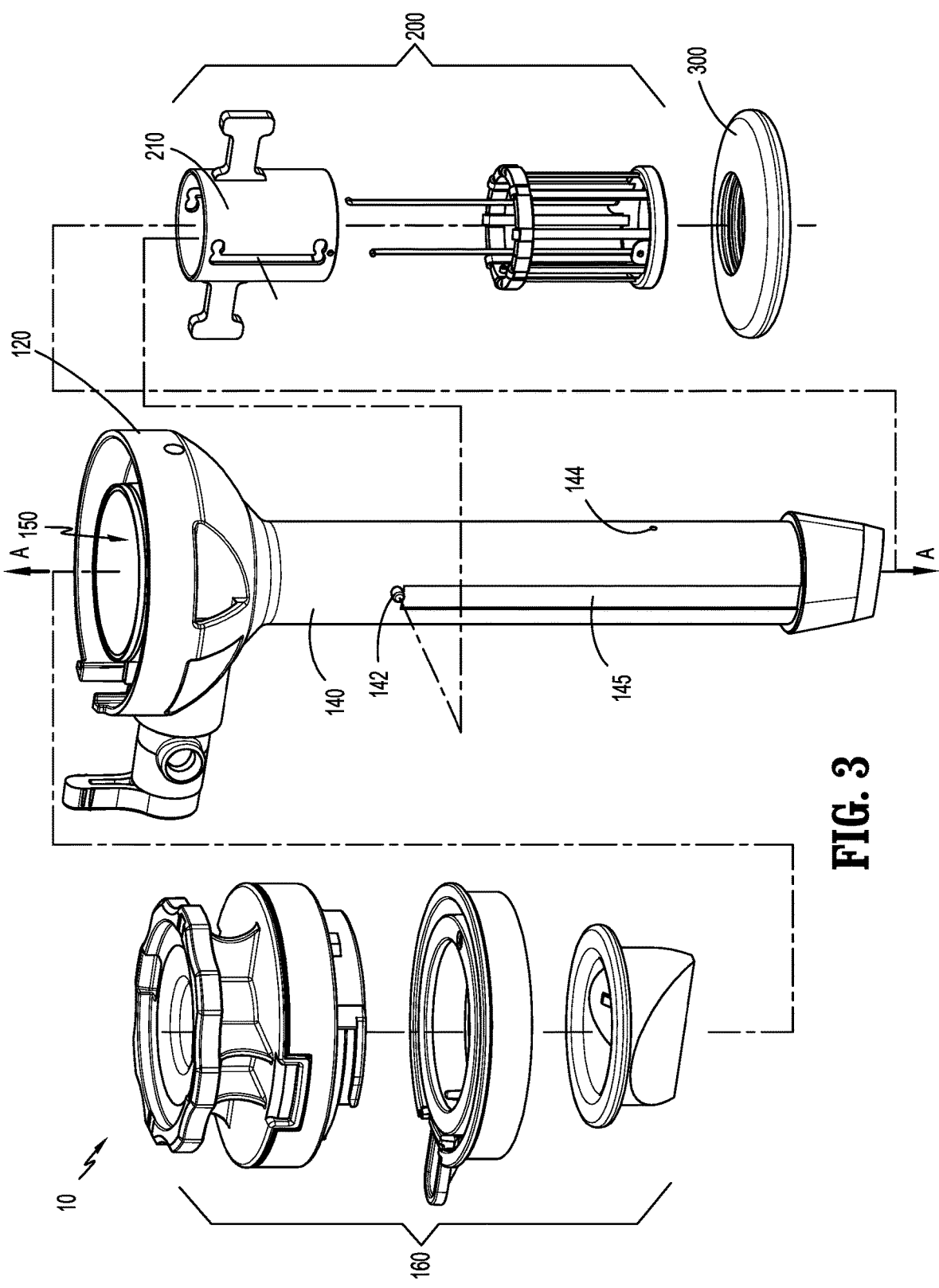
FIG. 3 is an assembly view of the surgical access device of FIG. 1.

With particular reference to FIGS. 2 and 5, each aperture of the pair of apertures 218 of the collar 210 is configured to engage a proximal finger 252 of each leg 251 of the driver 250, such that the collar 210 is fixed from longitudinal movement relative to the driver 250. The driver 250 also includes a pair of distal fingers 254 (one distal finger 254 at the distal end of each leg 251), each of which is configured to engage a respective aperture 232 of the distal ring 230 (FIG. 5). Accordingly, longitudinal translation of the collar 210 relative to the elongated portion 140 of the cannula body 100 results in a corresponding longitudinal translation of the driver 250, and a corresponding longitudinal translation of the distal ring 230. Additionally, rotational movement of the collar 210 about the longitudinal axis "A-A" relative to the elongated portion 140 results in a corresponding rotation of the driver 250, and a corresponding rotation of the distal ring 230. Further, the elongated portion 140 of the cannula body 100 includes a pair of slots 145 (one slot 145 is shown in FIG. 3), each slot 145 configured to allow one leg 251 of the driver 250 to be inserted therethrough.

With continued reference to FIGS. 2 and 5, the distal ring 230 encircles a portion of the elongated portion 140 of the cannula body 100, and includes a body 231, apertures 232 extending through respective tabs 233 which extend proximally from the body 231, and a plurality of grooves 234 (FIG. 5), each of which is configured to engage (e.g., fixedly engage) a distal end 242 of each petal of the plurality of petals 240.

The plurality of petals 240 is shown in FIGS. 2, 4, and 5, for example. The distal end 242 of each petal 240 is engaged (e.g., fixedly engaged) with the distal ring 230, and a proximal end 244 of each petal 240 is releasably engaged with the proximal ring 220. Further, and with particular reference to FIG. 2, the proximal end 244 of each petal 240 is hook-shaped, such that engagement between the proximal end 244 of the plurality of petals 240 and the proximal ring 220 hinders distal translation of the plurality of petals 240 (and thus the distal ring 230) relative to the proximal ring 220. The plurality of petals 240 may be made from metal, plastic or another suitable material, and are each biased (e.g., spring biased) away from the elongated portion 140 of the cannula body 100. Accordingly, when the plurality of petals 240 is moved proximally relative to the proximal ring 220 such that the proximal end 244 of each petal 240 is no longer restrained by the proximal ring 220, the proximal end 244 of each petal 240 moves in the general direction of arrow "F" (FIG. 7), away from the elongated portion 140.

Figure 7:
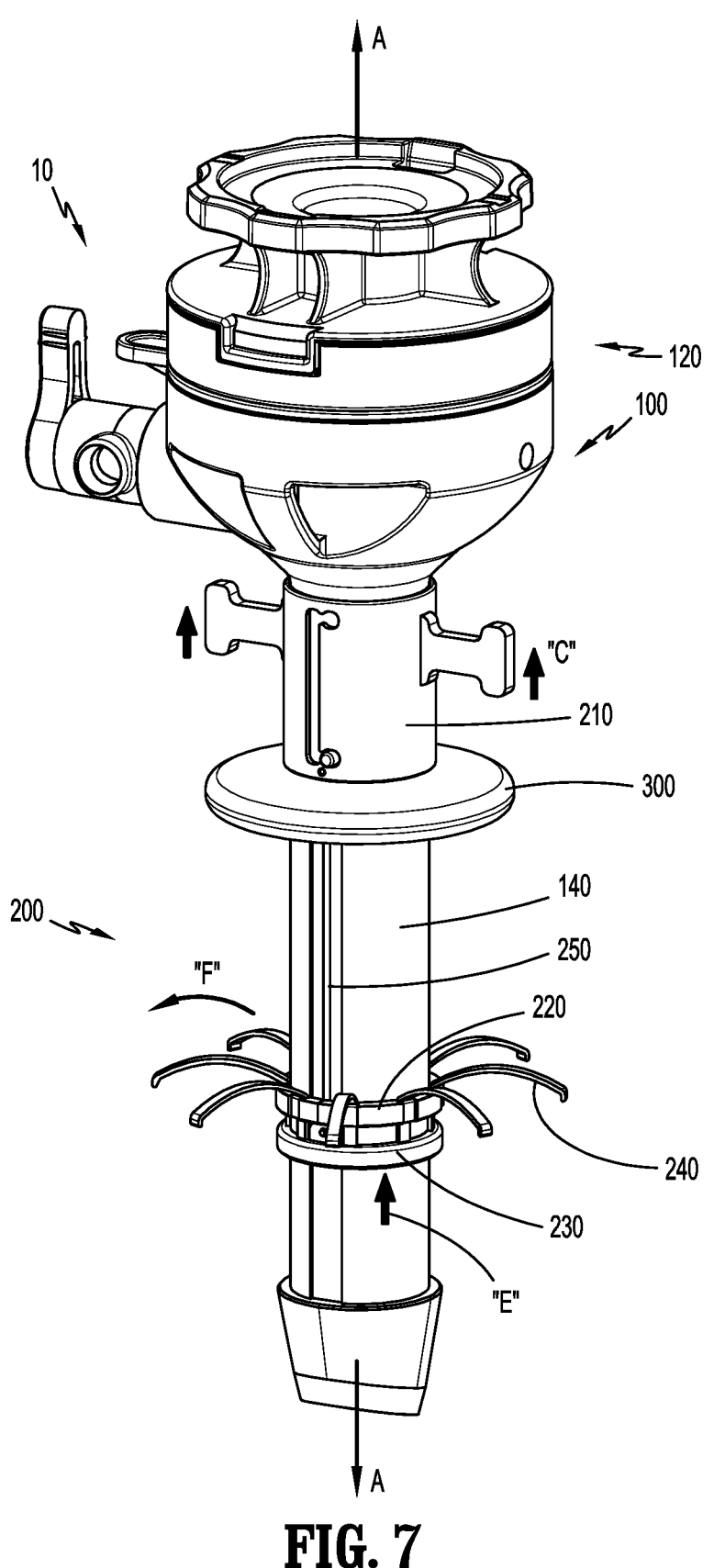
FIG. 7 is a perspective view of the surgical access device of FIG. 1 in a deployed configuration.
Figure 8:
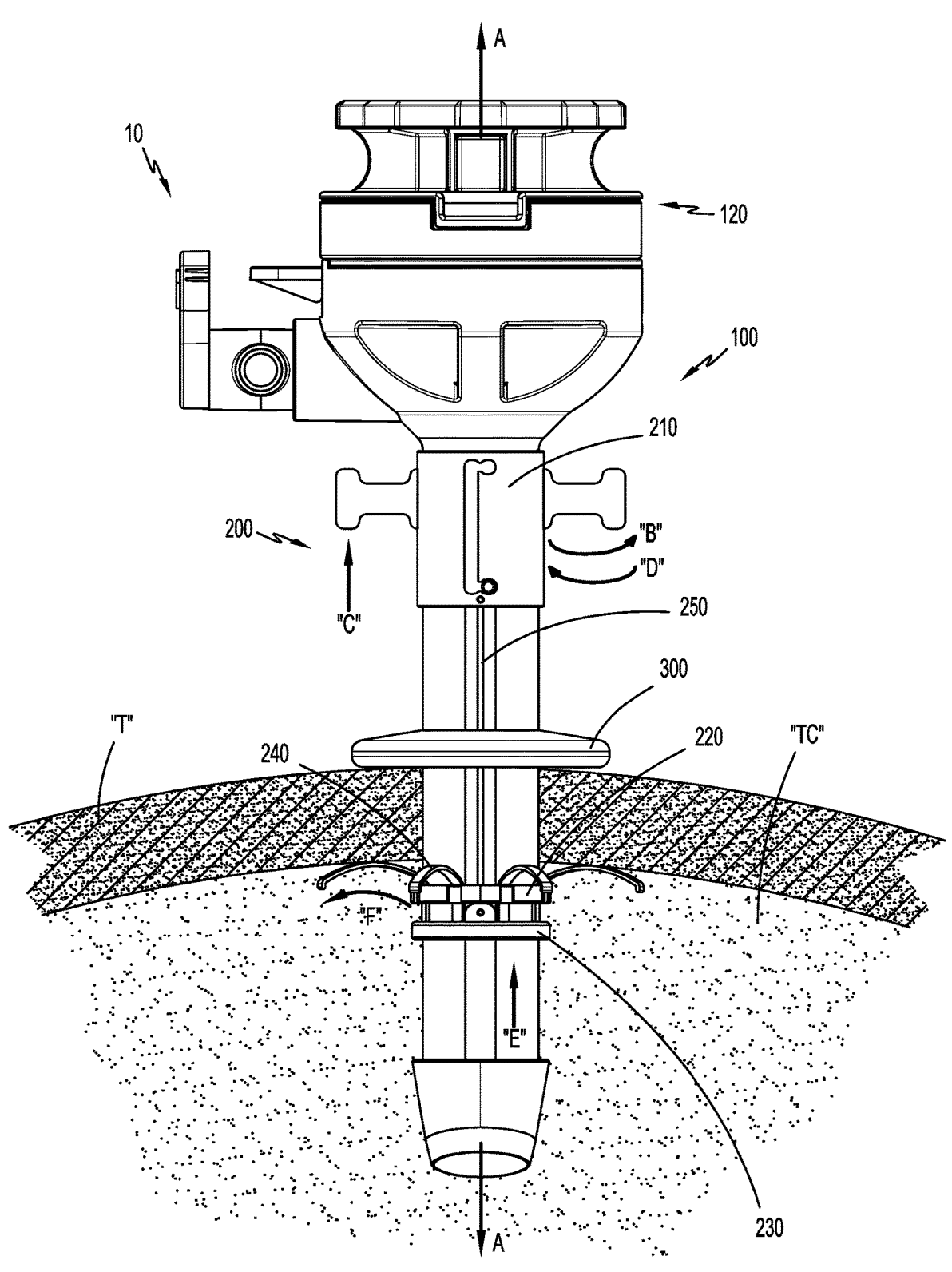
FIG. 8 is a side view of the surgical access device of FIG. 1 illustrating the fixation assembly within tissue in a deployed configuration.

More particularly, the plurality of petals 240 is movable between a first position (FIGS. 1-4 and 6) where the plurality of petals 240 is parallel or generally parallel to the longitudinal axis "A-A," and a second position (FIGS. 7 and 8) where each proximal portion 242 of each petal of the plurality of petals 240 flares away from the elongated portion 140 of the cannula body 100. When the plurality of petals 240 is in the first position, portions of the elongated portion 140 of the cannula body 100 (e.g., the portions located distally of an anchor 300) are insertable and removable from an opening in tissue. With particular reference to FIG. 8, in use, when the plurality of petals 240 of the fixation mechanism 200 is in the second position, the plurality of petals 240 is within the tissue cavity "TC" and is adjacent a distal portion of a tissue wall "T," thereby resisting a proximally-directed force acting on the surgical access device 10.

With particular reference to FIG. 5, the proximal ring 220 includes a first half 220a, and a second half 220b. The first half 220a of the proximal ring 220 includes a pair of apertures 222, which are each configured to engage a respective finger 224 of the second half 220b of the proximal ring 220. The engagement between the first half 220a and the second half 220b of the proximal ring 220 allow the proximal ring 220 to be assembled such that the proximal ring 220 radially surrounds the plurality of petals 240 and the elongated portion 140 of the cannula body 100. The proximal ring 220 also includes at least one radially inward-extending pin 226 configured to engage a respective aperture 144 (FIG. 3) of the elongated portion 140, thereby restricting longitudinal and rotational movement between the proximal ring 220 and the elongated portion 140.

Referring now to FIGS. 1-3 and 6-8, further details of the anchor 300 are shown. The anchor 300 is positionable around the elongated portion 140 of the cannula body 100 such that the anchor 300 radially surrounds a portion of the elongated portion 140. The anchor 300 can either have a frictional engagement with the elongated portion 140 such that the anchor 300 can be pushed/pulled to move between longitudinal positions, or the anchor 300 can be rotationally engaged with the elongated portion 140 (e.g., a threaded connection) such that the anchor 300 can be rotated about the longitudinal axis "A-A" relative to the elongated portion 140 to move between longitudinal positions. The anchor 300 may also be fixed from longitudinal and/or rotational movement relative to the elongated portion 140.

Figure 6:
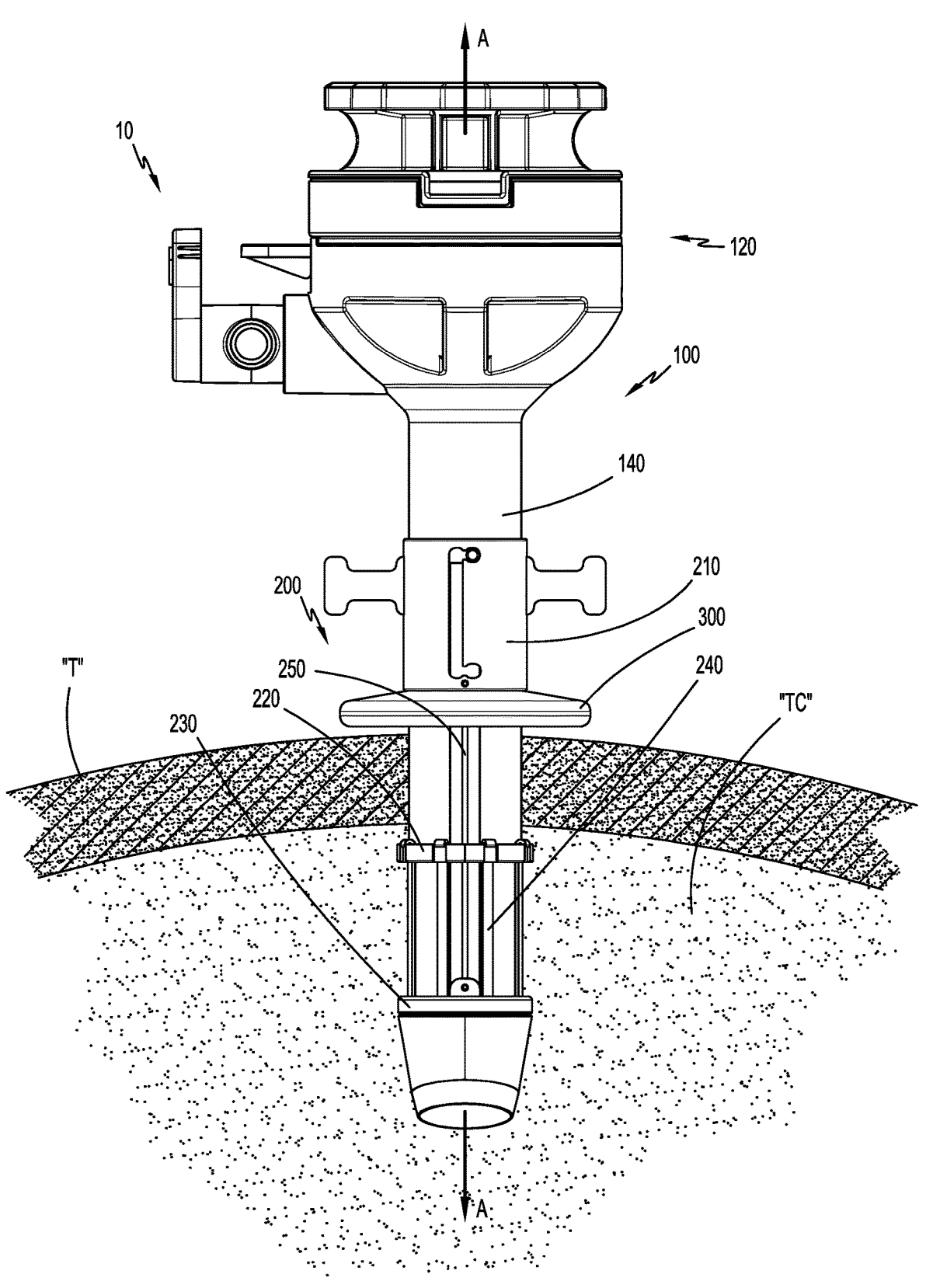
FIG. 6 is a side view of the surgical access device of FIG. 1 illustrating the fixation assembly within tissue in an undeployed configuration.

Referring now to FIGS. 6 and 8, in use, when the fixation mechanism 200 is in its first position (FIG. 6), corresponding to the collar 210 and the plurality of petals 240 being in their first positions, the distal end of the elongated portion 140 of the cannula body 100 is inserted through an incision "I" in tissue "T." Engagement between the anchor 300 and the proximal wall "PW" of the tissue "T" prevents additional insertion of the cannula body 100.

To transition the fixation mechanism 200 to its second position (FIG. 8), a user rotates the collar 210 in the general direction of arrow "B" relative to the elongated portion 140 of the cannula body 100, which pulls the collar 210 proximally in the general direction of arrow "C," then rotates the collar 210 in the general direction of arrow "D" relative to the elongated portion 140. This movement of the collar 210 relative to the elongated portion 140 causes the pins 142 of the elongated portion 140 to move within the respective slots 216 of the collar 210, from the proximal portion 216a (FIG. 6), through the connecting portion 216c, and into the distal portion 216b (FIG. 8). The proximal movement of the collar 210 also causes the driver 250, the distal ring 230, and the plurality of petals 240 to move proximally relative to the elongated portion 140 and relative to the proximal ring 220 in the general direction of arrow "E" (FIGS. 7 and 8). Further, as discussed above, the proximal movement of the plurality of petals 240 causes the proximal end 244 of each petal 240 to move in the general direction of arrow "F" in FIG. 7, away from the elongated portion 140. In this position, the surgical access device 10 can be moved proximally relatively to the tissue "T" such that the plurality of petals 140 engages a distal portion of the tissue wall "T," as shown in FIG. 8.

Next, in aspects where the anchor 300 is longitudinally movable relative the elongated portion 140 of the cannula body 100, the anchor 300 is moved distally such that the anchor 300 contacts a proximal portion of the tissue wall "T," thereby sandwiching the tissue wall "T" between the anchor 300 and the plurality of petals 240, and fixing the longitudinal position of the cannula body 100 relative to the tissue wall "T."

FIGS. 9-13 illustrate a surgical access device according to another aspect of the present disclosure. With initial reference to FIGS. 9 and 10, the surgical access device 500 includes a cannula body 1000 and a fixation mechanism 2000. The cannula body 1000 includes a proximal housing 1200 at its proximal end and includes an elongated portion 1400 extending distally from the proximal housing 1200. The elongated portion 1400 defines a channel 1500 (FIG. 10) extending therethrough, and defines a longitudinal axis "G-G." An obturator (not shown) is insertable through the channel 1500 and is engageable with the proximal housing 1200, for instance.

Figure 12:
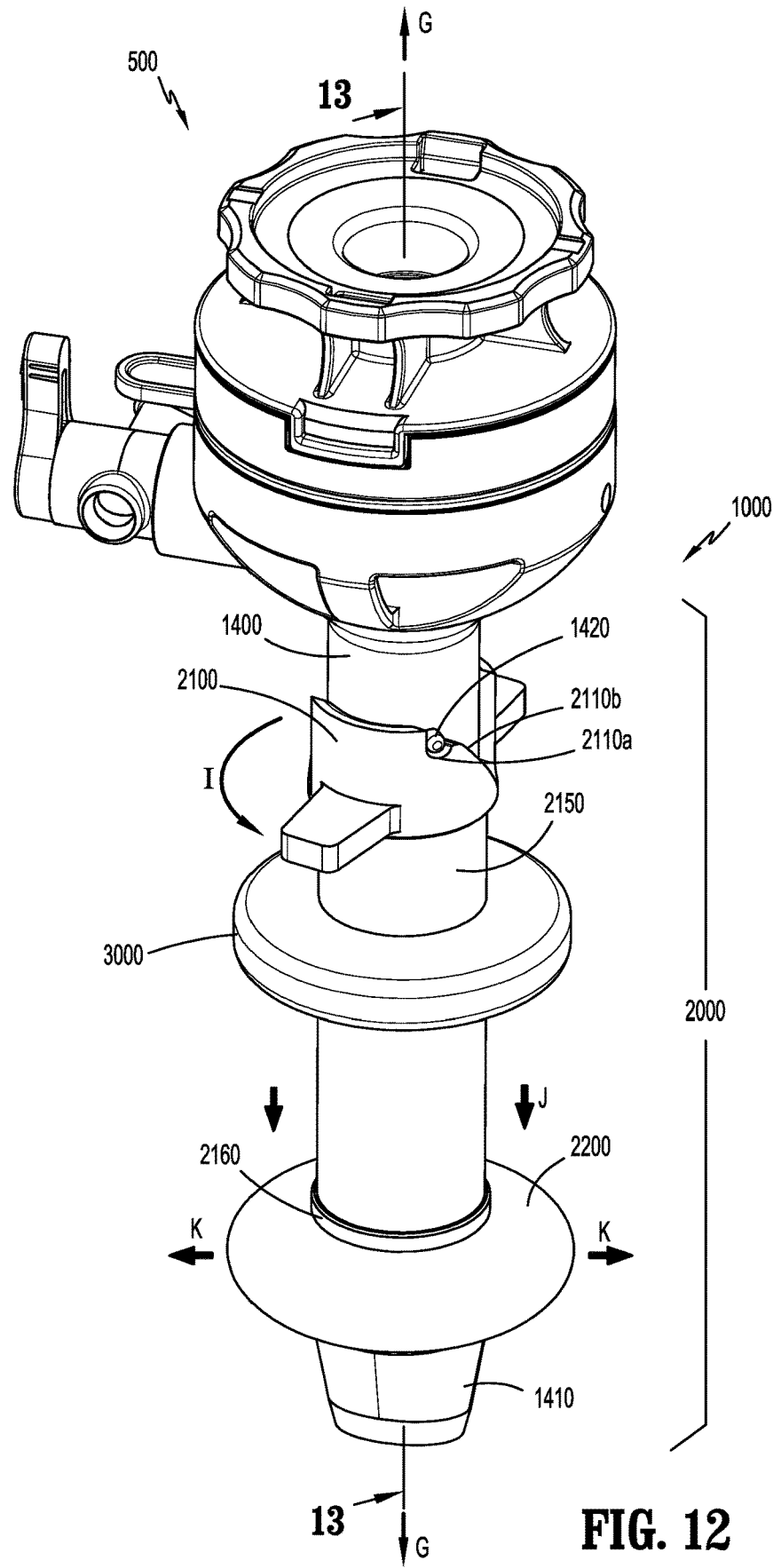
FIG. 12 is a perspective view of the surgical access device of FIG. 9 illustrating the fixation member in a deployed configuration.
Figure 13:
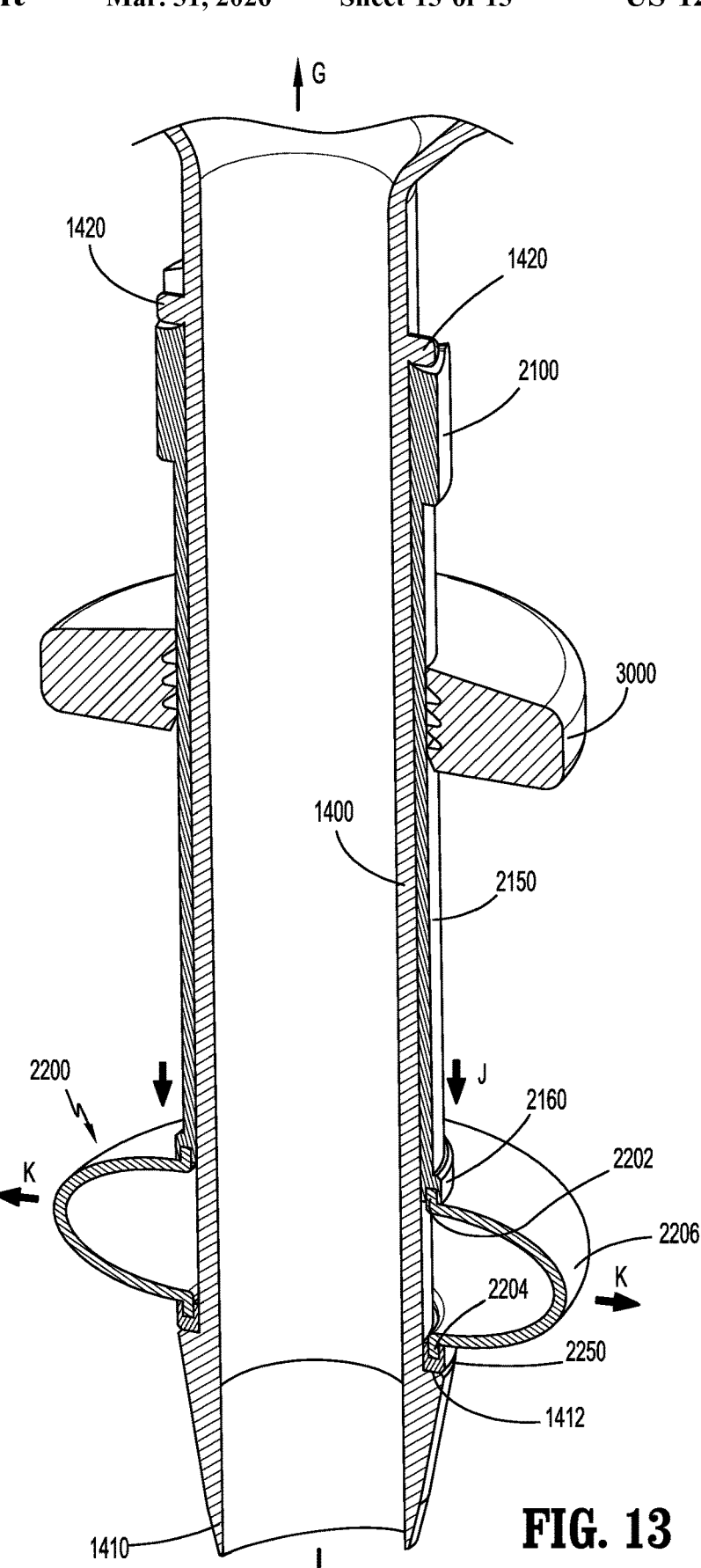
FIG. 13 is a longitudinal cross-sectional view of a portion of the surgical access device taken along line 13-13 in FIG. 12.

The fixation mechanism 2000 is positionable around the elongated portion 1400 of the cannula body 1000 such that such that the fixation mechanism 2000 radially surrounds a portion of the elongated portion 1400. More particularly, portions of the fixation mechanism 2000 are translatable longitudinally along the elongated portion 1400 between a first position, where a collar 2100 of the fixation mechanism 2000 is farther away from a distal tip 1410 of the elongated portion 1400 and where a portion of an expandable member 2200 of the fixation mechanism is closer to the longitudinal axis "G-G" (FIGS. 9 and 11), and a second position, wherein the collar 2100 is closer to the distal tip 1410 of the elongated portion 1400 and where the portion of the expandable member 2200 if farther away from the longitudinal axis "G-G" (FIGS. 12 and 13).

In various aspects, the expandable member 2200 is made of rubber. Such a rubber expandable member 2200 is able to retain its shape (in both the first position and the second position) without the need for the expandable member 2200 to be filled with fluid (e.g., liquid or gas), for instance.

Figure 9:
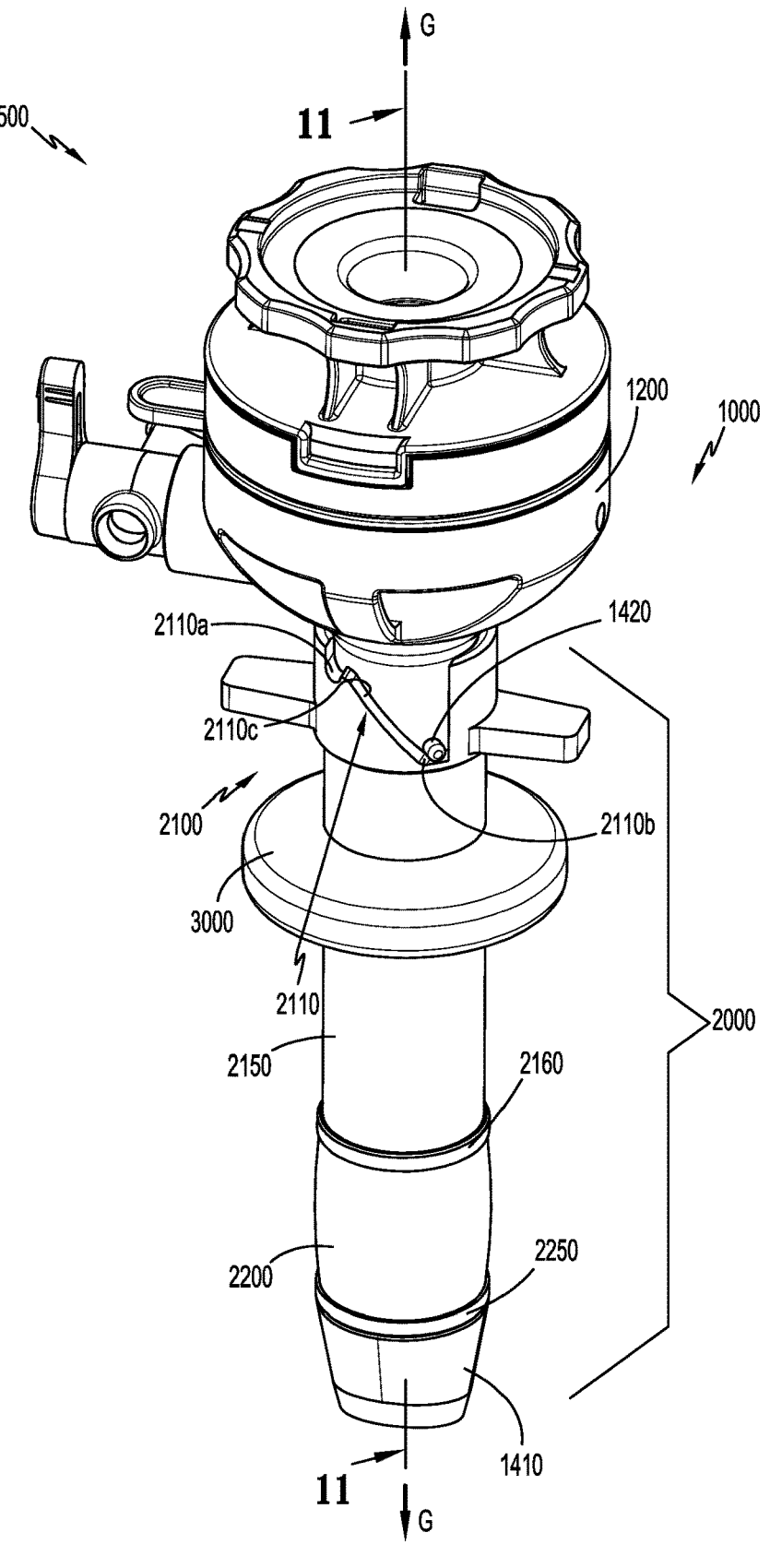
FIG. 9 is a perspective view of a surgical access device illustrating a fixation member in an undeployed configuration in accordance with a second aspect of the present disclosure.
Figure 10:
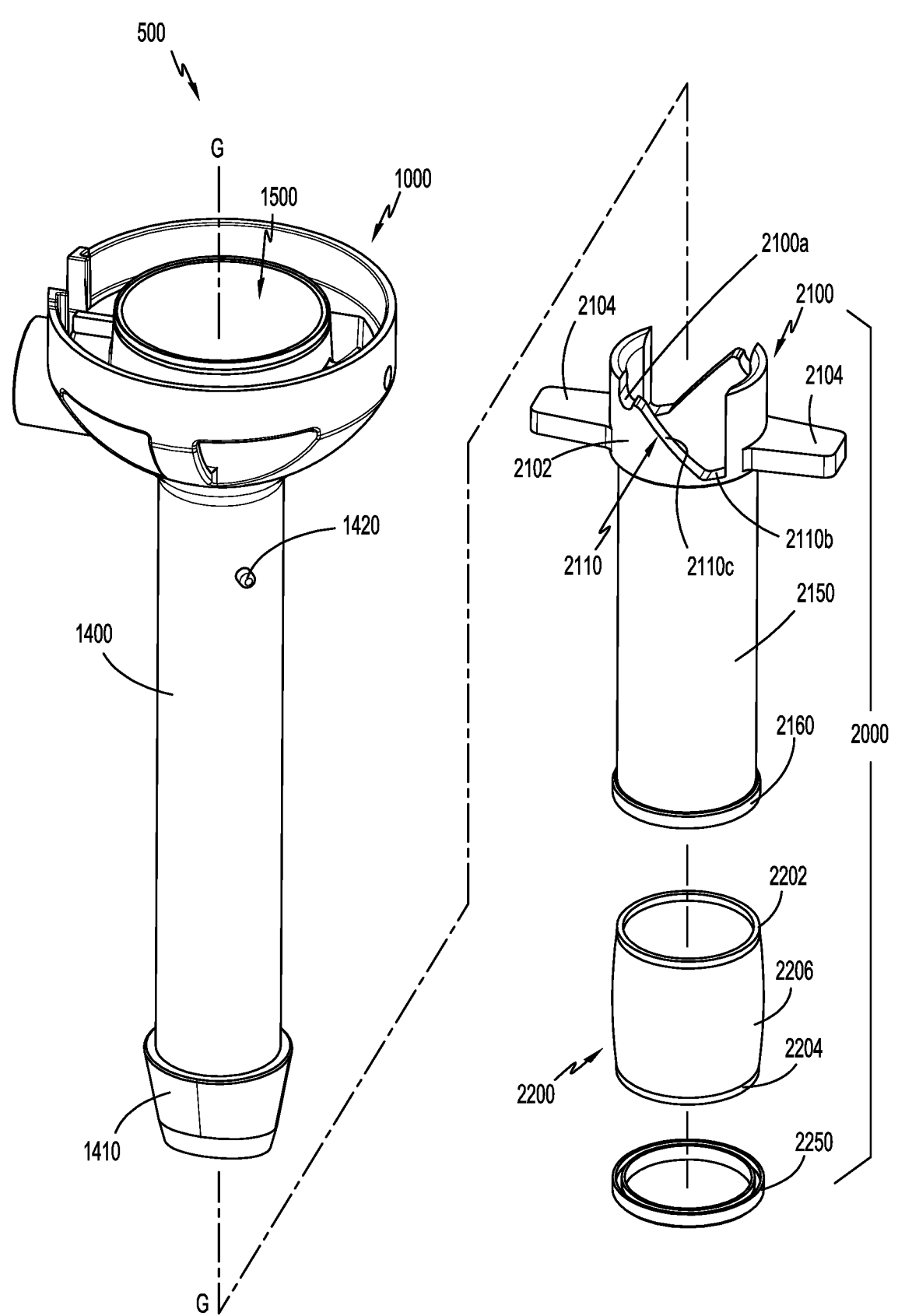
FIG. 10 is an assembly view of the surgical access device of FIG. 9.

Referring to FIGS. 9 and 10, the engagement between the fixation mechanism 2000 and the cannula body 1000 is shown. The fixation mechanism 2000 includes the collar 2100, a sleeve 2150 extending distally from the collar 2100, a proximal ring 2160 disposed at a distal end of the sleeve 2150, the expandable member 2200, and a distal ring 2250. A proximal end 2202 of the expandable member 2200 is engaged with (e.g., affixed to) the proximal ring 2160, and a distal end 2204 of the expandable member 2200 is engaged with (e.g., affixed to) the distal ring 2250.

The collar 2100, the sleeve 2150, and the proximal ring 2160 are longitudinally translatable relative to the elongated portion 1400 of the cannula body 1000 and are rotatable about the longitudinal axis "G-G" relative to the elongated portion 1400. The expandable member 2200 and the distal ring 2250 are also rotatable about the longitudinal axis "G-G" relative to the elongated portion 1400, but a lip 1412 (FIGS. 11 and 13) of the distal tip 1410 of the elongated portion 1400 restricts distal movement of the distal ring 2250 relative to the elongated portion 1400. As discussed in further detail below, distal movement of the proximal end 2202 of the expandable member 2200 relative to the elongated portion 1400 causes a middle portion 2206 of the expandable member 2200 to move away from the longitudinal axis "G-G."

With reference to FIGS. 9, 10, and 12, further details of the collar 2100 of the fixation mechanism 2000 are shown. The collar 2100 is a ring-like structure that radially surrounds a portion of the elongated portion 1400 of the cannula body 1000. The collar 2100 includes a body 2102, a pair of flanges 2104 extending radially outward from the body 2102, and a pair of cam surfaces 2110. The flanges 2104 are configured to be grasped by a user to facilitate rotating the collar 2100 about the longitudinal axis "G-G," and to facilitate longitudinally translating the collar 2100 in a direction parallel to the longitudinal axis "G-G."

Each cam surface of the pair of cam surfaces 2110 of the collar 2100 is configured to slidingly engage a respective pin 1420 extending radially outward from the elongated portion 1400 of the cannula body 1000. Each cam surface of the pair of cam surfaces 2110 includes a proximal portion 2110a, a distal portion 2110b, and a connecting portion 2110c, which interconnects the proximal portion 2110a and the distal portion 2110b (FIGS. 9, 10 and 12). Rotation and distal translation of the collar 2100 relative to the elongated portion 1400 causes the pair of cam surfaces 2110 to move relative to the pins 1420 from a first position where each pin 1420 is within the distal portion 2110b of each cam surface 2110 (FIG. 9), which corresponds to the expandable member 2200 being in the first, non-expanded position, to a second position where each pin 1420 is within the proximal portion 2110*a* of each cam surface 2110 (FIG. 12), which corresponds to the expandable member 2200 being in the second, expanded position.

Further, the collar 2100 is biased proximally into the first position (FIG. 9), such that the distal portion 2210*b* of the cam surface 2110 is urged into the pin 1420 of the elongated portion 1400 of the cannula body 1000, thereby restricting proximal movement of the collar 2100 relative to the elongated portion 1400. When the collar 2100 is in the second position (FIG. 12), the proximal portion 2210*a* of the cam surface 2110, which includes a valley, is urged into the pin 1420 of the elongated portion 1400 thereby restricting proximal movement of the collar 2100 relative to the elongated portion 1400. The connecting portion 2110*c* of the cam surface 2110 guides the movement of the collar 2100 relative to the pin 1420 between the first and second positions of the collar 2100.

The collar 2100 is fixedly engaged with the sleeve 2150, such that rotational and longitudinal movement of the collar 2100 translates to a corresponding rotational and longitudinal movement of the sleeve 2150. Additionally, the proximal ring 2160 is fixedly engaged with the sleeve 2150 such that rotational and longitudinal movement of the sleeve 2150 translates to a corresponding rotational and longitudinal movement of the proximal ring 2160.

Figure 11:
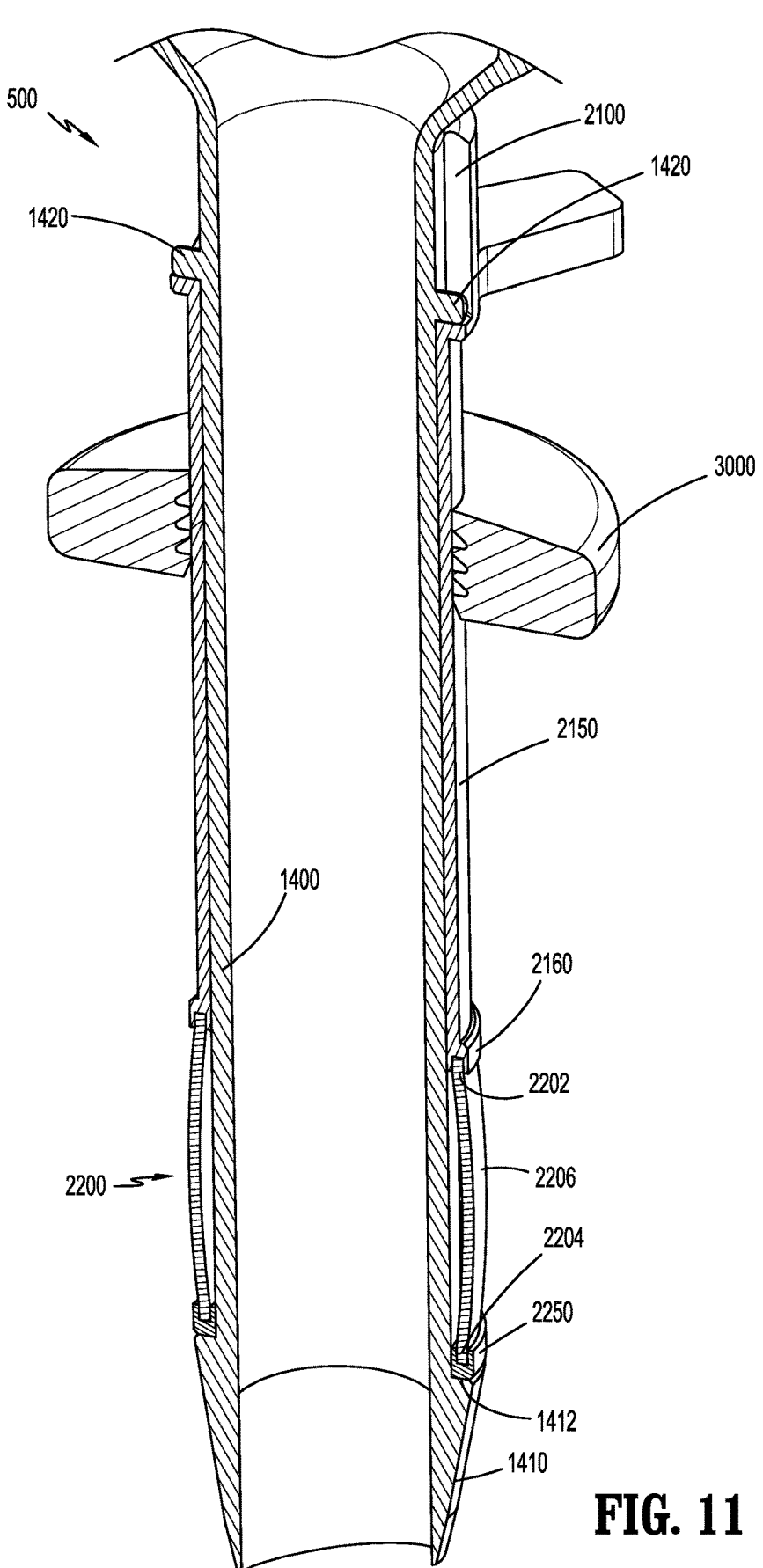
FIG. 11 is a longitudinal cross-sectional view of a portion of the surgical access device taken along line 11-11 in FIG. 9.

With particular reference to FIGS. 11 and 13, the expandable member 2200 is sandwiched between the proximal ring 2160 and the distal ring 2250. As noted above, the distal ring 2250 is fixed from moving distally relative to the elongated portion 1400 of the cannula body 1000 due to its engagement with the lip 1412 of the distal tip 1410 of the elongated portion 1400. Accordingly, as the proximal ring 2160 is moved distally, the expandable member 2200 becomes longitudinally compressed such that the expandable member 2200 moves from its first position (FIG. 11) where the middle portion 2206 of the expandable member 2200 is in contact with, close to or adjacent the elongated portion 1400, to its second position (FIG. 13) where the middle portion 2206 of the expandable member 2200 is farther away from the elongated portion 1400.

Referring now to FIGS. 9 and 11-13, an anchor 3000 is shown. The anchor 3000 is positionable around the elongated portion 1400 of the cannula body 1000 such that the anchor 3000 radially surrounds a portion of the elongated portion 1400. The anchor 3000 can either have a frictional engagement with the elongated portion 1400 such that the anchor 3000 can be pushed/pulled to move between longitudinal positions, or the anchor 3000 can be rotationally engaged with the elongated portion 1400 (e.g., a threaded connection) such that the anchor 3000 can be rotated about the longitudinal axis "G-G" relative to the elongated portion 1400 to move between longitudinal positions. The anchor 3000 may also be fixed from longitudinal and/or rotational movement relative to the elongated portion 1400.

With continued reference to FIGS. 9 and 11-13, in use, when the fixation mechanism 2000 is in its first position (FIGS. 9 and 11), corresponding to the collar 2100 and the expandable member 2200 being in their first positions, the distal tip 1410 of the elongated portion 1400 of the cannula body 1000 is inserted through an incision in tissue. Engagement between the anchor 3000 and a proximal wall of the tissue prevents additional insertion of the cannula body 1000.

To transition the fixation mechanism 2000 to its second position (FIGS. 12 and 13), a user rotates the collar 2100 in the general direction of arrow "I" (FIG. 12) relative to the elongated portion 1400 of the cannula body 1000, and (e.g., simultaneously) pushes the collar 2100 distally in the general direction of arrow "J" (FIGS. 12 and 13). This movement of the collar 2100 relative to the elongated portion 1400 causes the pins 1420 of the elongated portion 1400 to move along the respective cam surfaces 2110 of the collar 2100, from the distal portion 2110*b*, along the connecting portion 2110*c*, and into the proximal portion 2110*a* of the cam surfaces 2110. The distal movement of the collar 2100 also causes the sleeve 2150 and proximal ring 2160 to move distally relative to the elongated portion 1400 and relative to the distal ring 2250. Further, as discussed above, this distal movement causes the middle portion 2206 of the expandable member 2200 to move in the general direction of arrow "K" (FIGS. 12 and 13), away from the elongated portion 1400. In this position, the surgical access device 500 can be moved proximally relatively to the tissue such that the expandable member 2200 engages a distal portion of the tissue wall.

Next, in aspects where the anchor 3000 is longitudinally movable relative the elongated portion 1400 of the cannula body 1000, the anchor 3000 is moved distally such that the anchor 3000 contacts a proximal portion of the tissue wall, thereby sandwiching the tissue wall between the anchor 3000 and the expandable member 2200, and fixing the longitudinal position of the cannula body 1000 relative to the tissue wall.

While the above description contains many specifics, these specifics should not be construed as limitations on the scope of the present disclosure, but merely as illustrations of various aspects thereof. Therefore, the above description should not be construed as limiting, but merely as exemplifications of various aspects. Those skilled in the art will envision other modifications within the scope and spirit of the claims appended hereto.

What is claimed is:

1. A surgical access device, comprising:
a cannula body including a housing and an elongated portion extending distally from the housing, the elongated portion defining a longitudinal axis and a channel, the elongated portion including a pin; and
a fixation mechanism disposed in mechanical cooperation with the elongated portion of the cannula body, the fixation mechanism including:
a collar at least partially surrounding a first portion of the elongated portion of the cannula body, the collar being longitudinally translatable relative to the elongated portion of the cannula body, and being rotatable about the longitudinal axis relative to the elongated portion of the cannula body, the collar including a cam surface which slidingly engages the pin of the elongated portion;
a sleeve extending distally from the collar;
an expandable member extending distally from the sleeve and radially surrounding a second portion of the elongated portion of the cannula body; and
a distal ring engaged with a distal portion of the expandable member and being fixed from longitudinal translation relative to the elongated portion of the cannula body,
wherein distal translation of the collar relative to the elongated portion of the cannula body is configured to cause the expandable member to move from a first position defining a first gap between a middle portion of the expandable member and the elongated portion of the cannula body, to a second position defining a second gap between the middle portion of the expandable member and the elongated portion of the cannula body, the second gap being greater than the first gap.

2. The surgical access device according to claim 1, wherein the expandable member is made out of rubber.

3. The surgical access device according to claim 1, wherein the expandable member non-inflatably transitions between the first position and the second position.

4. The surgical access device according to claim 1, wherein the distal translation and a simultaneous rotation of the collar about the longitudinal axis relative to the elongated portion of the cannula body causes the expandable member to move from the first position to the second position.

5. The surgical access device according to claim 1, wherein the cam surface of the collar includes a proximal portion having a valley, an angled connecting portion, and a distal portion, the distal portion of the cam surface contacting the pin of the elongated portion of the cannula body when the expandable member is in the first position.

6. The surgical access device according to claim 5, wherein the valley of the cam surface of the collar portion contacts the pin of the elongated portion of the cannula body when the expandable member is in the second position.

7. The surgical access device according to claim 1, wherein proximal translation of the collar relative to the elongated portion of the cannula body causes the expandable member to move from the second position to the first position.

8. A surgical access device, comprising:

a cannula body including a housing and an elongated portion extending distally from the housing, the elongated portion defining a longitudinal axis and a channel, the elongated portion including a pin; and a collar at least partially surrounding a first portion of the elongated portion of the cannula body, the collar being longitudinally translatable relative to the elongated portion of the cannula body, the collar including a surface which slidingly engages the pin of the elongated portion;

a sleeve coupled to the collar; and an expandable member coupled to the sleeve and radially surrounding a second portion of the elongated portion of the cannula body, wherein translation of the collar relative to the elongated portion of the cannula body is configured to cause the expandable member to move from a first position defining a first gap between a middle portion of the expandable member and the elongated portion of the cannula body, to a second position defining a second gap between the middle portion of the expandable member and the elongated portion of the cannula body, the second gap being greater than the first gap, and wherein the translation, simultaneous with a rotation of the collar about the longitudinal axis relative to the elongated portion of the cannula body, causes the expandable member to move from the first position to the second position.

9. The surgical access device according to claim 8, further comprising a ring engaged with the expandable member, the ring being fixed from longitudinal translation relative to the elongated portion of the cannula body.

10. The surgical access device according to claim 9, wherein the ring is engaged with a distal end of the expandable member.

11. The surgical access device according to claim 8, wherein the sleeve extends distally from the collar.

12. The surgical access device according to claim 11, wherein the expandable member is coupled to a distal end of the sleeve.

13. The surgical access device according to claim 8, wherein the expandable member is made out of rubber.

14. The surgical access device according to claim 8, wherein the expandable member non-inflatably transitions between the first position and the second position.

* * * * *